US006180389B1

(12) United States Patent
Douglas et al.

(10) Patent No.: US 6,180,389 B1
(45) Date of Patent: Jan. 30, 2001

(54) VIRION-CONSTRAINED NANOPARTICLES COMPRISING A PLANT VIRION COAT PROTEIN SHELL AND ENCAPSULATED GUEST MOLECULES

(75) Inventors: Trevor Douglas, Billings; Mark J. Young, Bozeman, both of MT (US)

(73) Assignee: The Research and Development Institute, Inc., Bozeman, MT (US)

( * ) Notice: Under 35 U.S.C. 154(b), the term of this patent shall be extended for 0 days.

(21) Appl. No.: 08/775,366

(22) Filed: Jan. 3, 1997

(51) Int. Cl.$^7$ ........................................................ C12N 7/00
(52) U.S. Cl. ............................................ 435/235.1; 424/204.1
(58) Field of Search ................................ 435/235.1, 172.3, 435/236, 320.1; 530/350, 400, 412; 424/20.4, 274.1, 234.1, 600; 436/73

(56) References Cited

U.S. PATENT DOCUMENTS 5,358,722  10/1994  Monzyk ................................ 424/489
5,491,219  2/1996   Mann .................................. 530/391.1

OTHER PUBLICATIONS

T. Douglas et al. —Synthesis and Structure of an Iron(II) Sulfide–Ferritin Bioinorganic Nanocomposite—Science, vol. 269, 1995, p. 54–57.
Khazanovich et al. —Nanoscale Tubular Ensembles with Specified Internal Diameters. Design of a Self–Assembled Nanotube with a 13–Å Pore—J. Am. Chem. Soc. 1994, 116, 6011–6012.
Murphy, F., 1996, "Virus Taxonomy", in *Fields Virology*, Third Edition, Fields et al., eds., Lippincott–Raven Publishers, Philadelphia, P.A., pp. 23–48 and 51–54.*
Dong, J., et al., 1993, "Analysis of Retroviral Assembly Using a Vaccinia/T7–Polymerase Complementation System", Virol. 194:192–199.*
Douglas, T., 1996, "Biomimetic Synthesis of Nanoscale Particles in Organized Protein Cages", Biomimetic Mater. Chem., pp. 91–114.*
Houk, K.N., et al., 1996, "Gating as a Control Element in Constrictive Binding and Guest Release by Hemicarcerands", Science 273:627–629.*
Trevor Douglas, Biomimetic Synthesis of Nanoscale Particles in Organized Protein Cages, Chapter IV, Biomimetic Materials Chemistry, pp. 91–114.
Trevor Douglas et al., Synthesis and Structure of an Iron(III) Sulfide–Ferritin Bioinorganic Nanocomposite, Science, vol. 269, Jul. 7, 1995.

T. Douglas et al., "Inorganic—Protein Interactions in the Synthessis of a Ferrimagnetic Nanocomposite", Chapter 3, Hybrid Organic–Inorganic Composites, pp. 19–27.
Jeff W.M. Bulte et al., Magnetoferritin: Characterization of a Novel Superparamagnetic MR Contrast Agent, JMRI, May/Jun. 1994, vol. 4, No. 3, pp. 497–505.
Fiona C. Meldrum et al., Magnetoferritin: In Vitro Synthesis of a Novel Magnetic Protein, Science, vol. 257, Jul. 24, 1992, pp. 522–523.
Jeff W.M. Bulte et al., "Initial Assessment of Magnetoferritin Biokinetics and Proton Relaxation Enhancement in Rats", Acad. Radiol. 1995, vol. 2 No. 10, pp. 871–878.
Jeff W.M. Bulte et al., "Magnetoferritin, Biomineralization as a Novel Molecular Approach in the Design of Iron–Oxide–Based Magnetic Resonance Contrast Agents", Investigative Radiology, vol. 29, Supplement 2, S214–S216, 1994.
K.N. Houk, "Gating as a Control Element in Constrictive Binding and Guest Release by Hemicarcerands", Science, vol. 273, Aug. 2, 1996.
Kaehler, T., "Nanotechnology: Basic Concepts and Definitions", Clin. Chem. 1994; 40(9):1797–1799.*
Douglas et al., "Nanoparticles in Drug Delivery", in *Critical Reviews in Therapeutic Drug Carrier Systems*, CRC Press, 1987; 3(3):233–261.*
Douglas, T., "Biomimetic Synthesis of Nanoscale Particles in Organized Protein Cages", Biomimetic Materials Chemistry, 1996, pp. 91–114.*
Houk et al., "Gating as a Control Element in Constrictive Binding and Guest Release by Hemicarcerands", Science, 1996; 273:627–629.*
Zhao et al., "In Vitro Assembly of Cowpea Chlorotic Mottle Virus from Coat Protein Expressed in *Escherichia coli* and in Vitro–Transcribed Viral cDNA", Virol., 1995; 207:486–494.*
Dong et al., "Analysis of Retroviral Assembly Using a Vaccinia/T7–Polymerase Complementation System", Virol., 1993; 194:192–199.*

* cited by examiner

Primary Examiner—Laurie Scheiner
Assistant Examiner—Jeffrey S. Parkin
(74) Attorney, Agent, or Firm—McDermott, Will & Emery

(57) ABSTRACT

A virion-constrained nanoparticle of the invention comprises a shell of a virion coat protein(s) that encapsulates a core non-viral material, which is organic, inorganic or organometallic in nature. A particularly preferred virion coat is that of cowpea chlorotic mottle virus (CCMV). Encapsulation of a desired particle is effected by adjusting reaction conditions, e.g., by lowering the pH of a solution containing the virion protein and the non-viral substance. Processes for producing the virion-constrained nanoparticles of the invention are also described.

15 Claims, No Drawings

VIRION-CONSTRAINED NANOPARTICLES COMPRISING A PLANT VIRION COAT PROTEIN SHELL AND ENCAPSULATED GUEST MOLECULES

BACKGROUND OF THE INVENTION

The invention relates to novel nanoscale particles, methods of making same and uses thereof. More particularly, the invention relates to nanoscale particles which optionally are encased in a shell comprising one or more virion coat proteins, and methods associated therewith. In particular, the invention relates to virion-constrained nanoparticles comprising an inorganic, organic and/or organo-metallic material surrounded by a shell of one or more virion coat proteins. The invention further relates to methods of producing nanoscale particles, optionally through the use of controlled gating.

Ultrafine particles are useful in the production of many materials ranging, for example, from coatings, particularly coatings of one or more layers, to high performance lubricants, and from electronic devices to therapeutic delivery systems. Traditionally, fine particles have been prepared by grinding larger particles. However, such grinding results in a heterogeneous mix of particle sizes and shapes, and thus limits the usefulness of such particles. Such mixes can be further fractionated, for example, by passage though one or more sieves. In this case, the fractions collected may be in a certain size range, but within that range the size and shape distribution remains heterogeneous. Moreover, this additional size selection may result in a large amount of material that is discarded. Due to the disparity in particle shapes and sizes, discontinuities, stresses, frictions, etc. may arise in the resultant material, layer, lubricant, etc. for which the particles are employed. Thus, even after the expenditure of much effort in the prior art, suitable particles for high performance and high tolerance applications could not heretofore be reliably and economically produced by grinding methods.

Attempts to circumvent these problems have met with limited success in the past. These alternative approaches have included condensation of vaporized atoms and controlled precipitation of solutes out of solutions. In the case of precipitation where seed particles are used, the heterogeneity of the seed particles themselves render mixtures that are polydisperse. There is thus a need in the art for monodisperse particles of a desired size and/or shape.

Bunker, et al., "Ceramic Thin-Film Formation on Functionalized Interfaces Through Biomimetic Processing" Science 264: 48–55 (1994), discloses high density polycrystalline films of oxides, hydroxides and sulfides. These films are disclosed to be useful in a wide variety of applications. The films are prepared using substrates having functionalized surfaces. These surfaces are given a ceramic coating by the process of nucleation and particle growth mechanisms.

Aksay, et al., "*Biomimetic Pathways for Assembling Inorganic Thin Films,*" *Science* 273: 892 898 (1996) discloses a process whereby a supramolecular assembly of surfactant molecules at an organic-inorganic interface to template for condensation of an inorganic silica lattice. The technique is thought to be useful in the synthesis of inorganic composites with designed architecture at the nanometer scale.

Huo, et al., "Generalized Synthesis of Periodic Surfactant/Inorganic Composite Materials" Nature 368: 317–321 (1994), discloses the direct co-condensation of anionic inorganic species with cationic surfactants and the cooperative condensation of cationic inorganic species with anionic surfactants. The cooperative assembly of cationic inorganic species with cationic surfactants is also disclosed. The main driving force for this self-assembly is thought to be electrostatic. The technique is useful for synthesis of several different mesostructured phases.

Evans et al., "*Biomembrane Templates for Nanoscale Conduits and Networks,*" *Science* 273: 933–935 (1996) discloses the production of solid phase networks and conduits through the use of photochemical polymerization of long (20 to 200 nm) nanotubes. Nanotubes are formed by the mechanical retraction of a "feeder" vesicle after molecular bonding to a rigid substrate. Multiple nanotubes can be linked to form the networks and circuits.

Trau et al., "*Field-Induced Layering of Colloidal Crystals,*" *Science* 272: 706709 (1996) discloses an electrohydrodynamic method for preparing a precise assembly of two- and three-dimensional colloidal crystals on electrode surfaces. The technique disclosed uses electrophoresis, with deposition and arrangement of the particles on the electrode. The technique provides for mono- or multi-layer crystalline films. It is also mentioned that the technique may be used to assemble macromolecules such as proteins into two dimensional crystals.

Monnier et al., "*Cooperative Formation of Inorganic-Organic Interfaces in the Synthesis of Silicate Mesostructures,*" *Science* 261: 1299–1303 (1993)) discusses a theoretical model of the formation and morphologies of surfactant silicate mesostructures. The article proposes a model for the transformation of a surfactant silicate system from the lamellar mesophase to the hexagonal mesophase. The effect of pH and ionic strength on mesophase structure are also discussed.

In a recent development, U.S. Pat. Nos. 5,304,382, 5,358,722, and 5,491,219, disclose the use of apoferritin devoid of ferrihydride as another solution to the problem of producing small particles. These ferritin analogs consist of an apoferritin shell and an inorganic core, and are thought to be useful in the production of ultrafine particles for high performance ceramics, drug delivery, and other uses.

Ferritin is a protein involved in the regulation of iron in biological systems. In nature, ferritin consists of a protein shell, having 24 structurally equivalent protein subunits surrounding a near spherical core of hydrous ferric oxide ("ferrihydrite"). The core is disclosed as being any organic or inorganic material with the exception of ferrihydrite. Once a core has formed in the process of these patents, the protein coat can be removed and the freed core particles isolated. The process is disclosed as providing for particles approximately 5 to 8 nanometers in diameter. However, this system is size constrained, such that homogeneous particles of smaller or larger sizes are not possible.

A general review of systems employing the apoferritin/core nanoscale particle production system is provided by Douglas, "*Biomimetic Synthesis of Nanoscale Particles in Organized Protein Cages*," Biomimetic Materials Chemistry, S. Mann (ed.) VCH Publishers, New York (1996).

Additional information on the apoferritin/core system includes:

Douglas et al., "*Inorganic-Protein Interactions in the Synthesis of a Ferromagnetic Nanocomposite*," American Chemical Society, ACS Symposium Series: Hybrid Organic-Inorganic Composites, J. Mark, C. Y-C Lee, P. A. Bianconi (eds.) (1995) discloses the preparation of a ferrimagnetic iron oxide-protein composite comprising an apoferritin shell and iron oxide core. The core is said to consist of magnetite or maghemite, but was thought to be predominantly maghemite. This magnetoferritin is said to be ideal for bio-compatible nmr imaging, and other biological and medical applications.

Douglas et al., "Synthesis and Structure of an Iron(III) Sulfide-Ferritin Bioinorganic Nanocomposite," Science 269: 54–57 (1995) discloses production of iron sulfide cores inside ferritin shells via an in situ synthesis reaction. The cores are disclosed as a mostly amorphous sulfide consisting predominantly of Fe(III). Cores are described as a disordered array of edge-shared $FeS_2$ units. Native ferritin particles with sulfided cores are taught to contain between 500 and 3000 iron atom cores, most predominantly in the Fe(III) form. Douglas et al. further disclose that the biomimetic approach to the production of nanoparticles may be useful for biological sensors, drug carriers, and diagnostic and bioactive agents.

Bulte et al., "Magnetoferritin: Characterization of a Novel Superparamagnetic MR Contrast Agent," JMRI, May/June 1994, pp. 497–505, discloses use of horse spleen apoferritin to prepare nanoparticles having a ferritin shell and iron oxide core. The article discloses that novel materials with defined crystal size can be produced by "confined biomineralization within specific subunit compartments." The magnetoferritin produced in the technique described is said to be useful in the production of a nanometer-scale contrast agent for magnetic resonance imaging. Coupling of "bioactive substances" to the ferritin case is further disclosed. Such substances are taught to include antibody fragments and synthetic peptides, which may be useful in tissue-specific imaging.

Meldrum et al., "Magnetoferritin: In Vitro Synthesis of a Novel Magnetic Protein," Science 257: 522–523 (1992) discloses the preparation of magnetoferritin by incubation of apoferritin in a solution of Fe(II) and with slow oxidation. The process described resulted in the discrete, spherical nanometer (ca. 6.0 nm) core particles surrounded by a ferritin protein shell. The core was consistent with being either magnetite or maghemite, most likely magnetite. Possible uses for the magnetoferritin particles are disclosed as the following: (1) industrial applications, (2) study of magnetic behavior as a function of miniaturization, (3) elucidation of iron oxide biomineralization processes, (4) magnetic imaging of biological tissue, and (5) in separation procedures involving cell and antibody labeling.

Meldrum et al., "Reconstitution of Manganese Oxide Cores in Horse Spleen and Recombinant Ferritin," Journal of Inorganic Biochemistry, 58: 59–68 (1995) discloses the formation of MnOOH cores within the nanoscale cavity of ferritin. Ferritin reconstitution with MnOOH cores is taught to be a nonspecific pathway, and an "all or nothing effect" (i.e., either unmineralized or fully loaded). Different apoferritin sources were used: (1) horse spleen ferritin, (2) recombinant H- and L-chain homopolymers and (3) H-chain variants containing site-directed modifications at the ferroxidase and putative Fe nucleation centers. The particle cores are described as being amorphous, whereas particles formed in bulk solution under substantially the same conditions were crystalline.

Bulte et al., "Initial Assessment of Magnetoferritin Biokinetics and Proton Relations Enhancement in Rats," Acad. Radiol., 2: 871–878 (1995), discloses blood clearance, in vivo biodistribution and proton relaxation enhancement of magnetoferritin (1.4 mg Fe/kg) in nude rats carrying a xenografted human small cell lung carcinoma. The kinetics of blood clearance was biexponential with an initial half-life of 1.4 to 1.7 min and a longer component lasting several hours. Ex vivo relaxometry revealed uptake in the liver, spleen and lymph nodes when magnetoferritin was administered with or without a pre-injection of apoferritin. No involvement with ferritin receptors (displayed on the carcinoma) was seen. Magnetoferritin is said to be potentially useful as an imaging agent for liver, spleen and lymph nodes.

Bulte et al., "Magnetoferritin: Biomineralization as a Novel Molecular Approach in the Design of Iron-Oxide-Based Magnetic Resonance Contrast Agents," Investigative Radiobiology 20 (Supplement 2): S214-S216 (1994) reports on the magnetometry and magnetic resonance relaxometry of magnetoferritin. Magnetoferritin is described as a biocompatible magnetic resonance contrast agent. The publication further discloses that magnetoferritin has a convenient matrix for complexing a wide variety of bioactive substances and may provide a basis for a novel generation of biocompatible magnetopharmaceuticals.

However, as mentioned above, in each of these systems employing the apoferritin/core system, whereas the distribution of the nanoscale particles is substantially homogeneous, the size of the particles is constrained by the size of the ferritin cavity. Furthermore, the apoferritin/core system is restricted such that large molecules may not readily enter the protein. Additionally, the internal cavity of ferritin is restricted in size 8 nm or less.

In light of the state of the art, then, it is one object of the invention to provide new and improved nanoscale organic, inorganic and/or organo-metallic particles useful in high performance materials, such as ceramics, lubricants, semiconductors and catalysts.

Another object of the invention is to provide new and improved nanoscale organic, inorganic and/or organo-metallic particles useful in drug delivery, medical imaging and other medical applications.

Another object of the invention is to provide for new and improved nanoscale particles having a substantially homogeneous size distribution and a predetermined, preselected particle size.

Another object of the invention is to provide for methods of producing nanoscale particles through controlled gating of a virion capsid, allowing the controlled entrapment and/or release of organic, inorganic and/or organo-metallic nanoparticles.

Other objects of the invention include the methods of making organic, inorganic and organo-metallic nanoscale particles having a defined and homogeneous size distribution and shape, as well as methods of using the nanoscale particles so produced in the manufacture of useful articles and devices. These and other objects of the invention will become readily apparent to those skilled in the art from the detailed description of the invention that follows.

SUMMARY OF THE INVENTION

The invention provides virion-constrained nanoparticles, characterized by a homogeneous particle size distribution and homogeneous particle shape, the particles comprising an organic, inorganic and/or organo-metallic material surrounded by a shell of virion coat protein.

The invention further provides for methods of making virion-constrained nanoparticles comprising:
  a) providing an isolated and substantially pure coat protein(s) of a virion;
  b) incubating the coat protein(s) in solution under conditions that permit re-assembly of a virion capsid;

c) admixing the re-assembled virion with one or more organic, inorganic and/or organo-metallic materials under conditions that entrap the material, optionally through controlled gating, to provide virion-constrained nanoparticles surrounded by the virion coat protein(s); and d) isolating the virion-constrained nanoparticles produced, and optionally releasing the nanoparticles through controlled gating.

The invention additionally provides for methods of making virion-constrained nanoparticles comprising:

a) providing isolated and substantially pure coat protein(s) of a virion;

b) incubating the virion coat protein(s) in a solution comprising one or more organic, inorganic and/or organo-metallic materials under conditions that permit assembly of a virion and permit the virion to entrap the material, optionally by controlled gating, to provide virion-constrained nanoparticles surrounded by the virion coat protein(s); and, c) isolating the virion-constrained nanoparticles produced and, optionally releasing the nanoparticles by controlled gating.

The invention further provides for methods of making virion-constrained nanoparticles comprising:

a) providing an isolated and substantially pure virions devoid of viral nucleic acid;

b) incubating the virions in a solution comprising one or more organic, inorganic and/or organo-metallic materials under conditions that permit the virion to entrap the material, optionally by controlled gating, to provide virion-constrained nanoparticles surrounded by the virion; and c) isolating the virion-constrained nanoparticles produced and optionally releasing the nanoparticles through controlled gating.

DETAILED DESCRIPTION OF THE INVENTION

The invention provides a novel solution to the production of nanoscale particles of predetermined size and shape by advantageously employing the coat protein(s) of a virion to provide for a wide range of size-constrained reaction environments.

As meant in this application, "virions" should be understood to include prokaryotic, protozoan, algal, fungal and eukaryotic viruses and virus-like particles. Prokaryotic viruses include Plasmaviridae, SSV1 group viruses, Lipothrixviridae, Cystoviridae, Corticoviridae, Myoviridae, Siphoviridae, Podoviridae, Microviridae, Inoviridae and Leviviridae. Bacteriophage such as M13, MS2, lambda, phiX174 and the like are also virions under the invention.

Protozoan, algal and fungal virions under the invention include Phycod naviridae, Rhizidiovirus, Totiviridae and Partitiviridae.

Plant virions under the invention include Caulimovirus, Genimivirus I, II and III, Reoviridae, Cryptovirus I and II, Rhabdoviridae, Bunyaviridae, Carmovirus, Dianthovirus, Ilarvirus, Cucumovirus, Bromovirus, Comovirus, Fabavirus, Nepovirus, Hordeivirus, Tobravirus, Furovirus, Tobamovirus, Potexvirus, Capillovirus, Carlavirus, Potyvirus, Closterovirus, Maize Chlorotic Dwarf Virus, Marafivirus, Necrovirus, Parsnip Yellow Fleck Virus, Sobemovirus, Tombusvirus, Tymovirus, Bromovirus, Commelina Yellow Mottle Virus, and, in particular, Cowpea Chlorotic Mottle Virus (CCMV).

Virions of eukaryotic invertebrates under the invention include Poxviridae, Entomopoxviridae, Baculoviridae, Eubaculovirinae, Nudibaculovirinae, Polydnaviridae, Ichnovirus, Iridoviridae, Bracovirus, Parvoviridae, Flavivirdae, Togaviridae, Bunyaviridae, Rhabdoviridae, Reoviridae, Bimaviridae, Picornaviridae, Tetraviridae and Nodaviridae.

Virions of eukaryotic vertebrates include, Poxviridae, Chorodopoxvirinae, Hepadnaviridae, Herpesviridae, Iridoviridae, Adenoviridae, Papovaviridae, Parvoviridae, Reoviridae, Birnaviridae, Picornaviridae, Caliciviridae, Coronaviridae, Paramyxoviridae, Bunyaviridae, Toriviridae, Orthomyxoviridae, Arenaviridae, Togaviridae, Flaviviridae, Retroviridae, Rhabdoviridae and Filoviridae.

"Homogeneous size" under the invention means that the majority of the particles in a sample are of substantially the same size.

"Homogeneous shape" under the invention means that the majority of the particles in a sample are of substantially the same shape.

"Virion-constrained nanoparticle" under the invention refers to particles having dimensions substantially in the nanometer range, and comprising a collection of atoms and/or molecules ranging in number from 1 to the number that can fit inside the volume of the selected virion. Thus the maximum number of atoms and/or molecules under the invention in a "virion-constrained nanoparticle" is determined by the size of the nanoparticle and the size of the virion inner cavity.

"Controlled Gating" as meant herein is the controlled, reversible process leading to the formation of an opening large enough to allow atoms/molecules to enter and/or exit.

The invention is exemplified below using the coat protein of the cowpea chlorotic mottle virus (CCMV). This virus has an icosahedral structure approximately 286 angstroms in diameter and is composed of 180 identical protein subunits. (Speir et al., *Structure* 3: 63–78 (1995)). These subunits are themselves arranged into discrete hexamers and pentamers and self-assemble under the constraints of cubic symmetry to form a roughly spherical structure. The native virion undergoes a structural transition in response to changes in pH. (Bancroft et al., *Virology* 31: 354–379 (1967); Jacrot, *Mol. Biol.* 95: 433–466 (1975)). As the pH is raised from 5.0 to 7.0 the capsid swells, with an approximately 10 percent increase in diameter. This swelling also induces the formation of openings between the inside and outside of the virion which are approximately 20 angstroms in diameter. Upon lowering the pH, the swollen virion reversibly shrinks, closing off the large openings. Thus, the CCMV virion provides a model system in which a gating (i.e., the controlled, reversible opening and closing of the virion) can be readily and reversibly accomplished.

The CCMV coat protein has been modified to yield an extremely stable variant having inter-subunit disulfide linkages (the "cys mutant"). This variant undergoes structural changes in response to changing pH similar to that of the wild-type virion. However, this mutant is able to withstand extreme pH conditions without dissociation into its component subunits or loss of quaternary structure.

In one embodiment, the present invention makes use of virion coat protein gating to provide for a constrained reaction environment in which organic, inorganic and/or organo-metallic materials can be contained. By carrying out the synthesis of, for example, inorganic materials in the presence of a virion under conditions suitable for mineral formation, and taking into advantage the controllable conformational changes in the virion coat, the present invention provides for virion-constrained nanoparticles having a predetermined size and displaying a homogeneous size distribution.

One process of the invention for the production of virion-constrained nanoparticles comprises:

a) providing an isolated and substantially pure coat protein(s) of a virion;

b) incubating the coat protein(s) under solution conditions that permit re-assembly of a virion capsid;

c) admixing the re-assembled virions with one or more organic, inorganic and/or organo-metallic materials under solution conditions that promote entrapment of the material, optionally by gating, so as to provide for virion-constrained nanoparticles surrounded by the virion capsid; and, d) isolating the virion-constrained nanoparticles produced and optionally releasing said nanoparticles through controlled gating.

Another process of the invention for the production of virion-constrained nanoparticles comprises:

a) providing an isolated and substantially pure coat protein(s) of a virion;

b) incubating the coat protein(s) in a solution comprising one or more organic, inorganic and/or organo-metallic materials under solution conditions that permit virion assembly and promote entrapment of the material, optionally through controlled gating, so as to provide for virion-constrained nanoparticles surrounded by the virion; and, c) isolating the virion-constrained nanoparticles produced and optionally releasing said nanoparticles through controlled gating of the virion.

Yet another process of the invention for the production of virion-constrained nanoparticles comprises:

a) providing isolated and substantially pure virions;

b) incubating the virions in a solution comprising one or more organic, inorganic and/or organo-metallic materials under solution conditions that permit entrapment of the material, optionally through controlled gating, so as to provide for virion-constrained nanoparticles surrounded by the virion; and, c) isolating the virion-constrained nanoparticles produced and optionally releasing said nanoparticles through controlled gating.

In alternative embodiments, the virion-constrained nanoparticles so produced may be further incubated under solution conditions that promote removal of the proteinaceous material to provide virus-constrained nanoparticles comprising "naked" nanoparticle material.

The virion-constrained nanoparticles of the present invention have many utilities, such as in magnetic resonance imaging, contrasting agents, cell separation, drug delivery, semiconductor technology, magnetic memory materials for memory storage, precursors for ceramic coatings, seed crystals for bulk crystallization (such as $Fe_2O_3$), homogeneously sized high temperature lubricants (such as $Al_2O_3$), and the like.

The virion-constrained nanoparticles of the invention can comprise a variety of organic, inorganic and/or organo-metallic materials, ranging from single atoms and/or molecules to large conglomerates of the same. of inorganic species, the virion-constrained nanoparticles may include metal salts, metal oxides, non-metal oxides, metal and non-metal chalcogens, covalent solids such as iron oxide, coordination compounds, organo-metallic compounds, and the like. Monovalent and polyvalent metals can be advantageously used in the practice of the invention. For monovalent metal salts, silver chloride may be used to make virion-constrained nanoparticles useful for photography. Polyvalent metals include aluminum, barium, chromium, cobalt, copper, europium, gadolinium, lanthanum, magnesium, manganese, neodymium, titanium, yttrium, zirconium and the like. Radioactive isotopes of these and other metals, such as cobalt, uranium, technetium, iodine, and the like are also in some applications preferred (e.g., medical imaging and therapy). For some applications, it is desirable that the particle comprise an oxide, such as a hydrated oxide. For other applications it is desirable for the salt to comprise an anion such as acetate, bromide, carbonate, chloride, fluoride, iodide, nitrate, nitrite, oxalate, phosphate, phosphite, sulfate, sulfite and the like and mixtures thereof.

Organic molecules and salts thereof may also be used in the practice of the invention as the core material of the virion-constrained nanoparticles. Examples of such particles include nanoparticles of proteins and useful polypeptides, glycoproteins, sweeteners, such as sugars and aspartame, and other flavoring agents, wherein the particles are useful in, for example, the controlled release of the encapsulated material. Drugs and salts thereof, for example sodium acetylsalicylate and acetaminophen, may also be used to form the virion-constrained nanoparticle material for controlled release in a patient.

The concentration of the solute in the solution is maintained at levels to provide efficient entrapment. For example, where crystalline growth is desired, the solution is preferably maintained at saturation or supersaturation levels to provide for efficient crystal growth. As will be appreciated by those skilled in the art, this concentration will vary depending upon the solute/solvent employed. Alternatively, where interactions of the solute with the viral inner cavity are sufficiently strong, the empty virus particles may selectively partition the solute into the viral cavity and out of bulk solution.

In one embodiment of the invention, the shape of the virus-constrained nanoparticles can be determined by the inner cavity of the particular virion chosen. The cores comprise solid spherules in the case of CCMV, though the shape of the core is determined by the shape of the inner cavity of the particular virion chosen. Thus, for example, rod-like, elongate shaped particles, orate particles, etc., can be produced under the practice of the invention. Another highly useful feature of the invention is that the size of the virion-constrained nanoparticles can be predetermined merely by choice of virion used. Thus, particles substantially in the nanometer range can be obtained upon the suitable choice of virion.

The invention may be used in conjunction with any virus coat proteins that are capable of forming a constrained environment. These include both in vitro and in vivo viral coat protein constrained environments. In a preferred embodiment, the virions naturally can provide for gating, as in CCMV, under controllable and reproducible conditions to assist in the formation and, optionally, release of the virion-constrained nanoparticles. Controlled gating may be accomplished through, for example, changes in pH and/or ionic strength, the presence of metal ions and/or chelators, and the like. See generally Cram et al., "Container Molecules and Their Guests," Royal Society of Chemistry, Cambridge, England (1994) and Houk et al., *Science* 273: 627–629 (1996). However, it is to be understood that gating is not necessary to the practice of the invention.

The viral coat proteins may be modified such as to provide novel characteristics beneficial for use under the invention. For example, one or more amino acids comprising the inner wall of the virion cavity may be modified (e.g., by site-directed mutagenesis) to provide for novel chemical environments in the cavity. Thus, positive charge in the cavity may be increased through modifications adding, for example, additional lysine or arginine residues. Similarly, the negative charge of the cavity may be increased through, for example, the addition of the specifically placed glutamic and aspartic acid residues. In a like manner, the hydrophobicity of the cavity may be selectively altered through use of an appropriate substituted amino acid.

Chemical modifications and functionalization may also be used to modify the cavity environment. For example, the cavity may be modified by addition of thiols with the potential to form disulfides or react with metals (e.g., cadmium, gold).

Additionally, amino acids in the coat protein that are exposed on the outer surface of the particles may be modified to create novel properties. See U.S. Pat. No. 5,248,589. For example, such amino acid residues may be covalently linked to antibodies or fragments thereof, or other heterologous proteins, to provide for directed targeting of the virion-constrained nanoparticles to particular tissues in therapeutic and imaging techniques. As another example, the outer surface may be modified and/or functionalized with reactive groups that enhance interactions with surfaces. Covalent modifications to increase the stability of the virion particle or provide a site for further chemical modification, may also be used. Additional cysteine substitutions are particularly preferred in this embodiment.

The virion-constrained nanoparticles under the invention are also useful for providing certain ceramics having enhanced properties. Upon deposition on a substrate the particles can provide for two-dimensional crystal structure, yielding highly ordered monolayers and/or multi-layers, of the particle material. Upon subsequent treatment (e.g., heating, chemical modification, etc.) the particles may form monolayers providing a very smooth molecular surface on a substrate.

The virion-constrained nanoparticles of the invention are also useful in high tolerance lubricants. The lubricants under the invention are particularly useful in high heat conditions, such as, for example, engines. Moreover, when the lubricants of the invention are used in conjunction with the modified surfaces described above, molecularly smooth surface interactions can be obtained providing for very high performance systems. It thus can be seen that the virion-constrained nanoparticles of the invention provide many superior qualities and are useful in many applications, others of which will be appreciated by those skilled in the various arts.

EXAMPLE 1

The "cys mutant" virion (Fox et al., *Virology* 227: 229–233 (1997); Zhao et al., *Virology* 207: 486–494 (1995) is disassembled into its free protein and RNA components by dialysis of the virus particles at pH 7.5 in 500 mM $CaCl_2$ at 4° for about 18 hours. After dialysis, the RNA is separated from the coat protein by centrifugation. The recovered viral coat protein is re-assembled into empty particles by dialysis against 100 mM sodium acetate buffer (pH 5.0), 1 M sodium chloride at 4° C. for 18 hours. The resulting empty particles are further purified by banding on a continuous sucrose gradient.

The empty virions so isolated are then incubated with 0.4 M $Na_2WO_4$ at pH 7.0 for approximately one week. During this incubation time, bulk crystallization of the fluid is found to occur. The bulk crystals are centrifuged into a pellet and the supernatant is concentrated and washed at least five times with 10 volumes of 100 mM sodium acetate (pH 4.8).

EXAMPLE 2

Empty CCMV virions are prepared as in Example 1 and incubated at pH 7.5 (above the gating threshold) with the $WO_4^{-2}$ ions, followed by a slow decrease in pH through the slow diffusion of HCl gas. This embodiment of the invention has two complementary results. First, the tungstate undergoes oligomerization leading to precipitation in the bulk phase. Secondly, the pores of the swollen virion close, trapping the mineral inside. Thus, controlled gating is achieved in this instance, through the alteration of the solution pH. The bulk precipitation is removed by dissolution using a wash solution buffered to a pH below 6.5 (to ensure that the virion remains "closed"). The mineralized virion is then isolated by centrifugation, for example on a sucrose gradient.

After the preparation of virion-constrained nanoparticles, the samples are visualized using transmission electron microscopy and small electron dense cores are observed. These cores are the size expected based on the size of the internal cavity of the virion. Negative staining of the particles with uranyl acetate shows that the virion particles remain intact and that the electron dense cores are within the virion cavities.

The virion coat protein can also be expressed using recombinant DNA technology under another embodiment of the invention, thereby eliminating the need to separate the viral nucleic acid from the coat protein subunits. As an example of such recombinant expression, the skilled artisan may express the viral coat protein in *Escherichia coli*. (Zhao et al., *Virology* 207: 486–494 (1995)). However, any other expression system, including use of other bacterial strains, yeast, baculovirus, and mammalian expression systems may be used in this embodiment of the invention, as is recognized by those skilled in the art.

Each of the patents and publications referred to above are incorporated herein by reference.

While the invention has been described in conjunction with specific embodiments, it is evident that there are numerous variations which will be apparent to those skilled in the art in light of the foregoing description. Accordingly, the claims appended hereto are meant to be interpreted with the broad scope this novel and useful invention merits.

What is claimed is:

1. A virion-constrained nanoparticle comprising a plant virion coat protein shell surrounding a nanopartice of non-viral origin selected from the group consisting of organic, inorganic and organo-metallic materials.

2. The plant virion-constrained nanoparicle according to claim 1, wherein said nanoparticle of non-viral origin comprises an organic material.

3. The virion-constrained nanoparficle according to claim 1, wherein said nanoparticle of non-viral origin comprises an inorganic material.

4. The virion-constrained nanoparticle according to claim 1, wherein said nanoparticle of non-viral origin comprises an organo-metallic material.

5. A virion constrained nanoparticle according to claim 1, wherein said plant virion is selected from the group consisting of Caulimovirus, Genimivirus I, II, and III, Cryptovirus I and II, Carmovirus, Dianthovirus, Ilarvirus, Cucomovirus, Bromovirus, Comovirus, Fabavirus, Nepovirus, Hordeivirus, Tobravirus, Furovirus, Tobamovirus, Potexvirus, Capillovirus, Carlavirus, Potyvirus, Closterovirus, Maize Chlorotic Dwarf Virus, Marafivirus, Necrovirus, Parsnip Yellow Fleck Virus, Sobemovirus, Tombusvirus, Tymovirus, Bromovirus, Commelina Yellow Mottle Virus, and Cowpea Chlorotic Mottle Virus (CCMV).

6. The virion-constrained nanoparticle according to claim 1, wherein said virion coat protein is the cowpea chlorotic mottle virus coat protein.

7. A process for producing virion-constrained nanoparticles comprising a plant virion coat protein shell surrounding a nanopaxticle of non-viral origin comprising the following steps:
   a) providing isolated and substantially purified plant virion coat protein shells containing controllable gates;
   b) incubating the virion coat protein shell in a solution comprising one or more organic, inorganic, and/or organo-metallic materials under conditions that permit controlled entry of the materials into the virion shell;
   c) adjusting the solution conditions in such a manner that the virion coat protein shell entraps the materials of step b); and
   d) isolating the virion-constrained nanoparticles produced.

8. The process according to claim 7, wherein said coat protein of said virion is the cowpea chlorotic mottle virus coat protein.

9. The process according to claim 7, wherein said nanoparticle of non-viral origin comprises an organic material.

10. The process according to claim 7, wherein said nanoparticle of non-viral origin comprises an inorganic material.

11. The process according to claim 7, wherein said nanloparticle of non-viral origin comprises an organo-metallic material.

12. A process according to claim 7, wherein said plant virion is selected from the group consisting of Caulimovirus, Genimivirus I, II, and III, Cryptovirus I and II, Carmovirus, Dianthovirus, Ilarvirus, Cucomovirus, Bromovirus, Comovirus, Fabavirus, Nepovirus, Hordeivirus, Tobravirus, Furovirus, Tobamovirus, Potexvirus, Capillovirus, Carlavirus, Potyvirus, Closterovirus, Maize Chlorotic Dwarf Virus, Marafivirus, Necrovirus, Parsnip Yellow Fleck Virus, Sobemovirus, Tombusvirus, Tymovirus, Bromovirus, Commelina Yellow Mottle Virus, and Cowpea Chlorotic Mottle Virus (CCMV).

13. A process according to claim 7, wherein the adjustment of one or more conditions is selected from the group consisting of changes in pH, changes in ionic strength, the presence of metal ions, and the presence of chelators.

14. A process according to claim 7, wherein said non-virial nanoparticle is an inorganic mnaterial sclected from the group consisting of metal salts, metal oxides, non-metal oxides, metal chalcogens, non-metal chalcogens, covalent solids, and coordination compounds.

15. A process according to claim 7, wherein said non-viral nanoparticle is an organic material selected from the group consisting of polypeptides, glyco proteins, sweeteners, flavoring agents, drugs and salts thereof.

* * * * *